(12) United States Patent
Hill et al.

(10) Patent No.: US 8,846,108 B2
(45) Date of Patent: *Sep. 30, 2014

(54) ANTIMICROBIAL BODY AFFECTING PRODUCTS

(75) Inventors: John Hill, Plymouth, MN (US); Joseph A. King, Wayzata, MN (US)

(73) Assignee: King Technology, Inc., Hopkins, MN (US)

( * ) Notice: Subject to any disclaimer, the term of this patent is extended or adjusted under 35 U.S.C. 154(b) by 589 days.

This patent is subject to a terminal disclaimer.

(21) Appl. No.: 12/592,693

(22) Filed: Dec. 1, 2009

(65) Prior Publication Data

US 2010/0143495 A1 Jun. 10, 2010

Related U.S. Application Data

(60) Provisional application No. 61/201,321, filed on Dec. 8, 2008.

(51) Int. Cl.
- *A01N 59/16* (2006.01)
- *A01P 1/00* (2006.01)
- *A61L 9/01* (2006.01)
- *A61L 2/16* (2006.01)
- *A01N 59/20* (2006.01)
- *C02F 1/50* (2006.01)

(52) U.S. Cl.
CPC . *A61L 2/16* (2013.01); *A01N 59/16* (2013.01); *A61L 9/01* (2013.01); *C02F 1/505* (2013.01); *A01N 59/20* (2013.01)
USPC ........................................................ 424/618

(58) Field of Classification Search
None
See application file for complete search history.

(56) References Cited

U.S. PATENT DOCUMENTS

| | | | | |
|---|---|---|---|---|
| 3,830,824 A * | 8/1974 | Margraf | ......................... | 548/101 |
| 3,830,908 A * | 8/1974 | Klippel et al. | ................ | 424/447 |
| 3,856,805 A * | 12/1974 | Margraf | ........................ | 548/109 |
| 3,930,000 A | 12/1975 | Margraf | | |
| 3,932,627 A * | 1/1976 | Margraf | ........................... | 514/56 |
| 5,298,624 A * | 3/1994 | Lasker | ........................... | 548/107 |
| 7,347,934 B2 * | 3/2008 | King et al. | ................. | 210/198.1 |
| 2002/0172709 A1 | 11/2002 | Nielsen | | |
| 2006/0043011 A1 * | 3/2006 | King et al. | ................. | 210/198.1 |
| 2008/0156739 A1 * | 7/2008 | King | ............................ | 210/749 |

FOREIGN PATENT DOCUMENTS

| | | |
|---|---|---|
| WO | WO0009173 | 2/2000 |
| WO | WO 02/26039 A1 * | 4/2002 |
| WO | WO2008085499 | 7/2008 |

* cited by examiner

*Primary Examiner* — Abigail Fisher
*Assistant Examiner* — Daniel L Branson
(74) *Attorney, Agent, or Firm* — Jacobson & Johnson LLC

(57) ABSTRACT

A method and apparatus for control the growth of microorganisms by enhancing the concentration metal ions therein. The method includes the step of to enhancing the effectiveness of an antimicrobial agent having a source of metal ions by adding a compound containing a hydantoin ring to the antimicrobial agent.

18 Claims, 5 Drawing Sheets

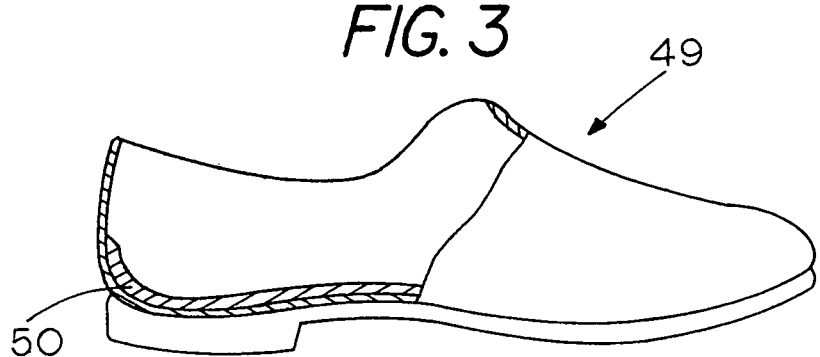
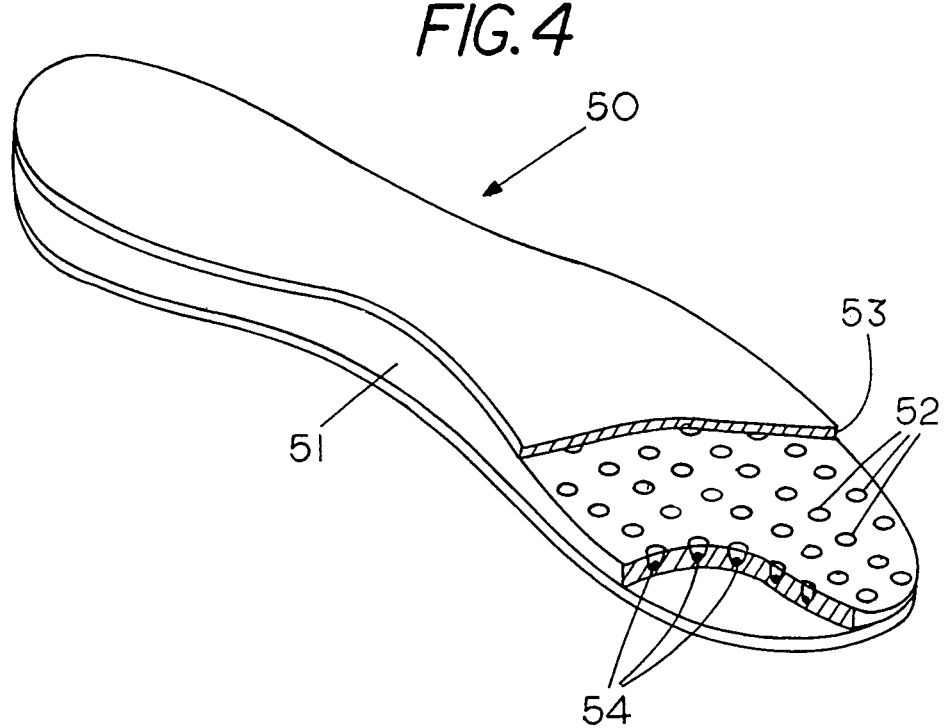

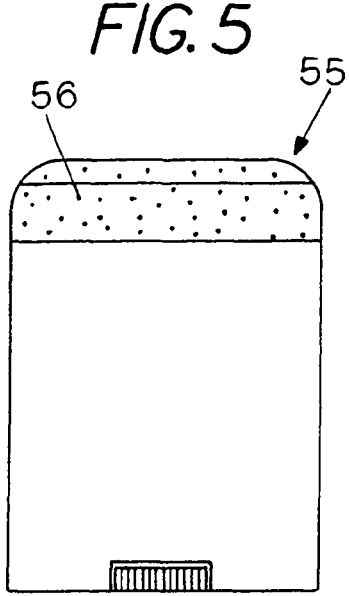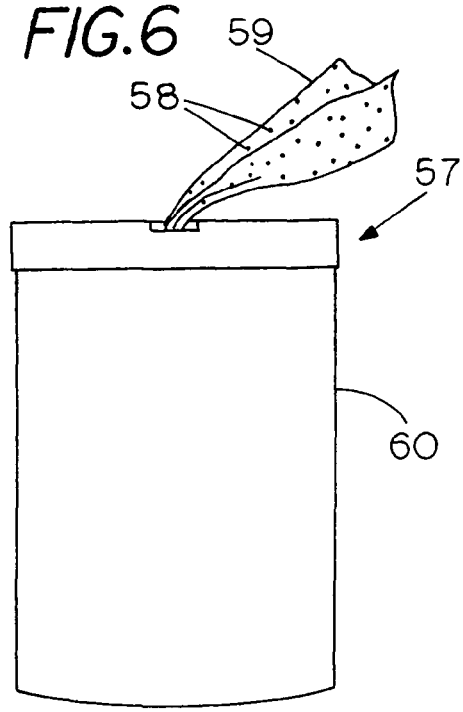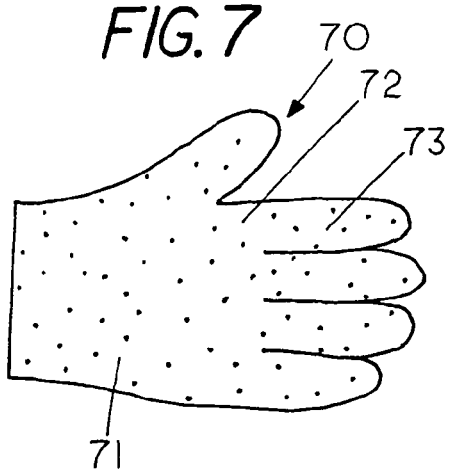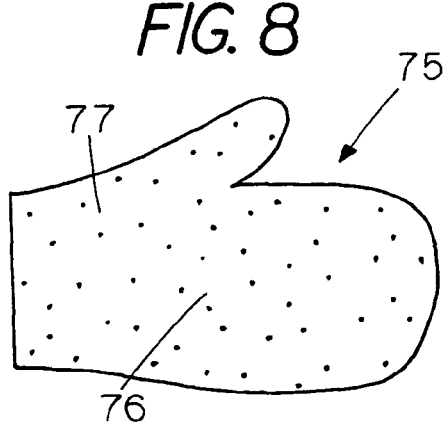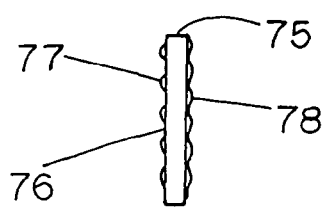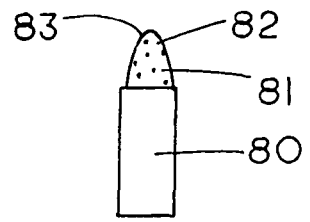

Dissolved Silver Concentrations

| Date | Solution C (with DMH) Ag(ppb) | Solution D (without DMH) Ag(ppb) | Ratio |
|---|---|---|---|
| Date | Start | Start | Start |
| Week One | 4.3 | 2.8 | 2 |
| Week Two | 17 | 8.7 | 2 |
| Week Three | 46 | 2.4 | 19 |
| Week Four | 86 | 2.9 | 30 |
| Week Five | 140 | 4.0 | 35 |
| Week Six | 220 | 7.1 | 31 |
| Average | 86 | 4.7 | 18 |

ANTIMICROBIAL BODY AFFECTING PRODUCTS

CROSS REFERENCE TO RELATED APPLICATIONS

This application claims priority from U.S. provisional application 61/201,321 filed Dec. 8, 2008 titled Products With Sanitizers.

FIELD OF THE INVENTION

This invention relates generally to antimicrobial body affecting products and, more specifically, to the incorporation of an antimicrobial agent onto or into body affecting products to eliminate or control the growth of microorganisms.

STATEMENT REGARDING FEDERALLY SPONSORED RESEARCH OR DEVELOPMENT

None

REFERENCE TO A MICROFICHE APPENDIX

None

BACKGROUND OF THE INVENTION

One of the concerns for individuals and businesses is the presence of harmful bacteria and toxins in both a home environment and a business environment as well as the need to preserve materials from decay or decomposition. It is known that bacteria and other microorganisms can remain in an active state on structure surfaces for an extended length of time. The presence of water can cause the bacteria and other harmful microorganism to rapidly increase. As a result it becomes more likely that bacteria and other harmful microorganisms can be transferred from individual to individual through physical contact with the structure surfaces carrying the bacteria and other harmful microorganisms. It is also evident that the bacteria and harmful organisms can cause decay and decomposition. It is known that antimicrobial agents, which contain metal ions, can be incorporated into products to provide antimicrobial surfaces that release metal ions when contacted by a fluid. However, one of the disadvantages of such products is that the release of metal ions becomes limited by the solubility of the metal ions in the fluid.

In order to minimize the transfer of bacteria and other harmful microorganism through contact with body surfaces the invention described herein provides an antimicrobial agent that can be incorporated into body affecting products to reduce or eliminate harmful bacteria and other harmful microorganisms through releasing higher levels of antimicrobial metal ions from the known antimicrobial agents.

SUMMARY OF THE INVENTION

Briefly, the present invention comprises antimicrobial body affecting products that either directly or indirectly contact the user. The antimicrobial body affecting products eliminate or prevent growth of harmful microorganisms proximate the user including preventing bacteria and other harmful microorganisms from indirectly being transferred to a user through airflow.

The method for enhancing the health and safety of body products through a liquid activateable antimicrobial agent containing a source of biocidal metal ions which includes a compound containing a hydantoin ring wherein the liquid activated antimicrobial agent can kill or prevent growth of harmful microorganisms through increasing the availability of biocidal metal ions.

BRIEF DESCRIPTION OF THE DRAWINGS

FIG. 3 shows a partial cross-sectional view of a shoe incorporating an antimicrobial insole;

FIG. 4 shows a close-up view of the antimicrobial insole of FIG. 3;

FIG. 5 shows an antimicrobial deodorant that includes a source of biocidal metal and a compound containing a hydantoin ring for providing extended antimicrobial effects;

FIG. 6 shows antimicrobial hand wipes having a source of biocidal metal and a compound containing a hydantoin ring for providing instant antimicrobial effects;

FIG. 7 shows a glove containing a source of biocidal metal and a compound containing a hydantoin ring for providing hand antimicrobial effects;

FIG. 8 shows a one-piece hand shaped sheet of material containing a source of biocidal metal and a compound containing a hydantoin ring for providing hand antimicrobial effects on one side and an adhesive on the other side;

FIG. 9 shows an end view of the one-piece hand shaped sheet of FIG. 8;

FIG. 10 shows a tube of lipstick containing the antimicrobial agent;

DESCRIPTION OF THE PREFERRED EMBODIMENT

Figure 1:
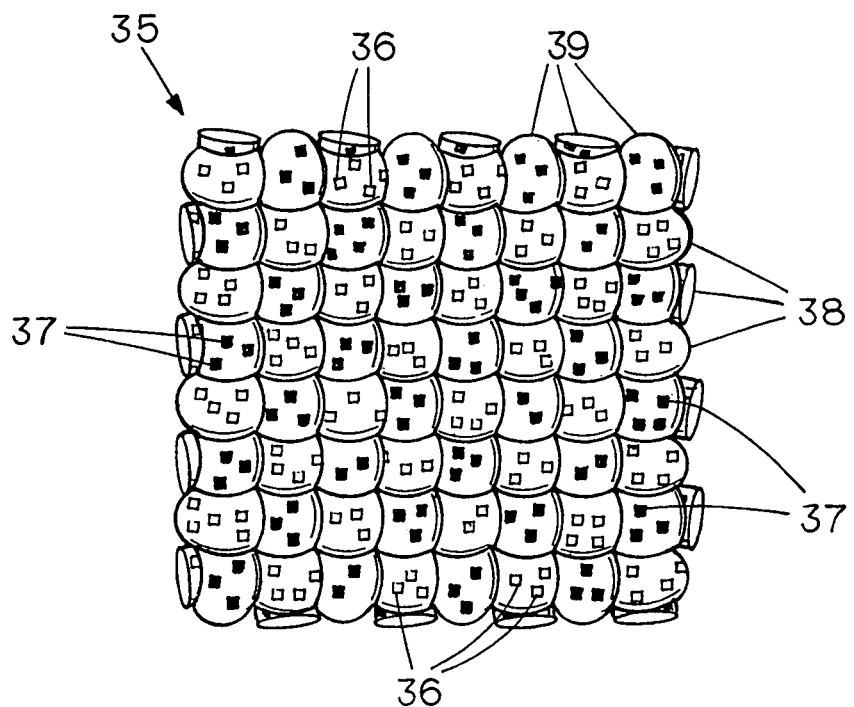
FIG. 1 is a close-up view showing an antimicrobial woven textile having a source of biocidal metal and a compound containing a hydantoin dispersibly secured thereto.

Surfaces that may be exposed to a supply of fluids or moist environments oftentimes provide for an avenue for harmful microbal growth. Several types of microbes are naturally present in fluids and may breed exponentially through time. The use of biocidal metals, such as silver or the like, that release heavy metals ions has been found to be an effective way of eliminating or controlling harmful microorganism, such as bacteria, in fluids. In one example, a biocidal metal ion such as a silver ion is used to kill microbes in fluids proximate the biocidal metal ion. However, the solubility of various metallic ions such as silver ion in liquids, such as water, limits the available silver ions and hence the effectiveness in quickly and effectively killing microbes. For example, due to the nature of silver ions in readily complexing with other components or compounds, it is often difficult to maintain silver ions in a antimicrobial active form for long durations.

Tests have revealed that a antimicrobial agent containing a biocidal metal ion source and a compound containing a hydantoin ring have the ability to interact with metal ion donors including silver metal ion donors such as silver bromide to increase the solubility of the silver in a liquid and thus aid in the killing harmful microorganisms without use of any additional antimicrobial agent. For example, it has been discovered that with a silver ion donor in the presence of DMH in a fluid such as water, the dissolved silver concentrations are higher than anticipated when compared to a control solution without the presence of DMH. In addition, the silver concentration increases with time. The results suggested that DMH interacts with silver to form a soluble complex even if the source(s) of silver are from insoluble salts such as silver bromide, which in some cases may be derived from silver chloride. In the process described herein the effectiveness of the antimicrobial metal ions, particularly the silver ions, is obtained through increasing the solubility of the silver by addition of a compound containing a hydantoin ring which may or may not have any antimicrobial effect.

In one example the invention is directed to the field of anti-microbial compositions and to methods of reducing microbe numbers on direct body products such as clothing by applying or incorporating the antimicrobial agent therein. In particular, the invention is directed to the incorporation or application of the antimicrobial agent into the clothing or a garment that comes into direct contact with a human. The antimicrobial agent may be incorporated or applied to the body products such as articles of wear through methods such as soaking or spraying a liquid solution of the sanitizer on the clothing or to applying the sanitizer to the fabrics before the fabrics are made into clothing, however, the methods of application are for illustrative purposes and no limitation is intended thereto.

In another example the antimicrobial agent may be in an on demand condition after being applied to garments or incorporated in garments that later become exposed to body fluids Examples include various clothing articles wherein the activating liquids are the body fluids such as sweat.

In another example the antimicrobial agent may be applied to or incorporated in products that are directly applied to or upon a surface of the human body including but not limited to body products such as deodorants, various feminine products, shampoo/conditioner, lipstick, facial creams.

In another example the antimicrobial agent may be applied or incorporated in body cleaning products such as hand or facial wipes.

In another example the antimicrobial agent may be applied or used in moist environments such as found in air conditioner filters and fluid collection pans as well as dehumidifiers to eliminate or prevent the growth of a microorganism in the fluid in the air conditioners an the dehumidifiers to prevent airflow therepast from brining the harmful microorganisms into body contact. Controlling the growth of a microorganism as used herein is intended to encompass effecting diminished proliferation and/or lethal results to microorganisms including but not limited to bacteria, spores, yeast, fungi, mold and multi-cellular microorganisms.

U.S. Pat. No. 6,821,936 teaches that silver-containing inorganic micro-biocides have recently been developed and utilized as antimicrobial agents on and within a numerous substrates and surfaces. In particular, such micro-biocides have been adapted for incorporation within melt spun synthetic fibers. However, such melt spun fibers are expensive to manufacture due to the large amounts of silver-based compound required to provide sufficient antimicrobial activity in relation to the migratory characteristics of such a compound within the fiber itself to its surface.

For textile, the composition is especially aimed at controlling and/or eliminating malodor generated by microbes and mold from clothing articles and fabrics. The malodor generating microbes generally originate from the presence of fluids such as bodily fluids, sweat, urine, and vomit, dampness, and mildew. The textiles include materials made of natural fibers, such as cotton and wool, regenerated natural fibers including regenerated cellulose, and materials made of synthetic organic fibers, such as acetate, polyacrylics, polyamides, polyester fibers, polyolefins, polyvinylidene chlorides, and/or rayon, and combinations thereof. Illustrative examples of textiles include carpets, upholstery, drapes, and fabrics such as clothing and furniture coverings. One of the features of the invention is to solve the above problems by enhancing the effectiveness of the silver-based compound to provide sufficient antimicrobial activity thereby limiting cost by requiring the use of lower amounts of the silver-based compound.

FIG. 1 is a close-up view showing an antimicrobial woven textile 35 having a bacteria killing material comprising a source of biocidal metal ions and a compound containing a hydantoin ring with both dispersibly adhered to the surface of the woven textile 35. The source of biocidal metal ions functions to release biocidal metal ions into a fluid proximate thereto to effectively kill or control microorganisms in the fluid. The addition of compound containing a hydantoin ring, which may or may not, have any antimicrobial properties to the biocidal metal ions has been found to increases the presence of biocidal metal ions to levels that are greater than if only the biocidal metal ions were used without the compound containing a hydantoin ring.

In the example shown, the source of biocidal metal comprises silver chloride 36 directly secured to a first set of fibers 38 of the woven textile 35 and the source of the compound containing a hydantoin ring is 5,5-dimethylhydantoin (DMH) 37 which is directly secured to a second set of fibers 39 of the woven textile 35. Although silver chloride will be discussed hereinafter as an example of a source of biocidal metal and DMH will be discussed hereinafter as an example of a source of a compound containing a hydantoin ring, other sources of biocidal metals and hydantoins may also be used. As an alternative both the silver chloride and the compound containing the hydantoin ring may be adhered to the same fiber.

Figure 2:
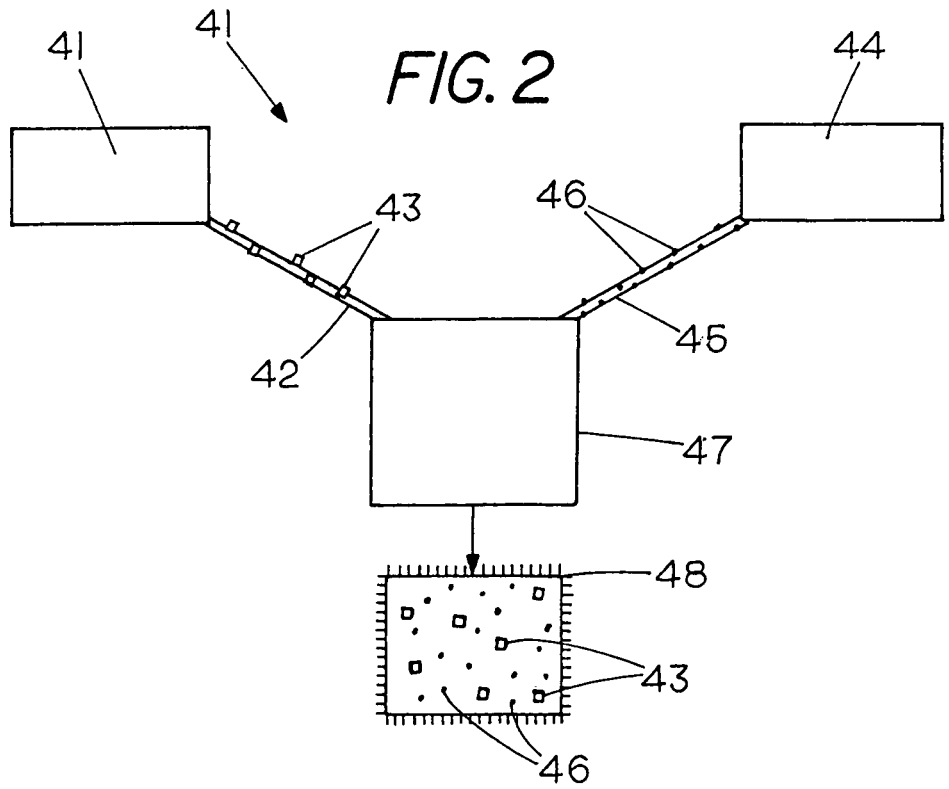
FIG. 2 shows a textile manufacturing system for forming the antimicrobial woven textile of FIG. 1.

FIG. 2 shows a textile manufacturing system 40 for forming the antimicrobial woven textile 35 of FIG. 1 comprising the securement of the silver chloride 36 and the DMH 37 on the fibers 38 and 39 before the fibers 38 and 39 are woven into the textile 35. More specifically, textile manufacturing system 40 includes a first station 41 for forming a fiber 42 having silver chloride particles 43 secured thereto. A second station 44 includes a second fiber 45 having DMH particles 46 secured thereto. The fiber are directed into a third station 47 that weaves the fibers into a textile 48 comprised of fibers with the silver chloride particles 43 thereon and fibers with the DMH particles 46 thereon which are located in proximity to each other to thereby release silver ions into a fluid to effectively kill or control microorganisms in the fluid when contacted by the fluid while also releasing DMH when contacted by a fluid containing the silver ions to maintain a higher silver ion level in the fluid in killing microorganisms than if silver ions from the silver chloride were used alone in killing microorganisms in the fluid.

While biocidal metals and the hydantoins are shown adhered to the exterior of the fibers 42 and 45 the biocidal metals and the compound containing a hydantoin ring may also be embedded in the fibers 42 and 45 rather than adhered to the exterior of the fibers 42 and 45.

In use, when woven textile 35 comes into contact with a source of fluid such as body fluids, including sweat or urine the silver chloride in the first set of fibers 38 releases silver ions into the fluid to effectively kill or control the growth of microorganisms. The DMH in the fluid increases the biocidal effectiveness of the silver by forming a complex with the silver to allow the silver to remain soluble to a higher degree thereby increasing the silver's antimicrobial activity.

It is noted that a feature of the invention is that the DMH and silver chloride provides for extended sanitation life as the DMH and silver chloride soluble complex is not formed until the presence of a fluid source. That is, the interaction between the DMH and silver chloride occurs after the DMH and silver chloride come in contact with a fluid. Although silver chloride has been described as example of source of a heavy metal ion other sources of heavy metal ions may be used.

Thus, fabric articles having a surface for growth of harmful microorganism which can directly or indirectly transmit harmful organism to a human can become more effective antimicrobial surfaces by including both a source of biocidal metal ions and a compound containing a hydantoin ring proximate the article surface whereby the presence a liquid releases biocidal metal ions into the fluid to thereby kill microorganisms on or proximate the article surface even though the compound containing a hydantoin ring may not have any antimicrobial properties.

Foot odor and infection are common problems caused by the growth of microbes in the enclosed environment of the shoe. Moisture resulting from foot perspiration provides an ideal growth environment for both bacteria and fungus, causing odor and athlete's foot. The inhibition of such growth of microbes has been a goal of the shoe industry. One of the approaches that have been used is to incorporate activated charcoal into a shoe insole in order to absorb odor and moisture. Although effective in controlling odor, the degree of moisture absorption is not sufficient to inhibit microbes growth thus odor continues to be produced and athlete's foot and other infections can occur. In addition, the ability of the activated charcoal to absorb odor is limited resulting in the short-live effectiveness of the insole.

Antimicrobial agents have also been incorporated within a shoe insole. However, the anti-microbes agents used often times are released too rapidly to provide for long-term effectiveness. Thus, it is desirable to provide articles and methods for delivering deodorants and antimicrobial compositions to the shoe environment during use in which the compositions last over numerous wearing of the shoes.

Referring to FIGS. 3 and 4, FIG. 3 shows a partial cross-sectional view of a shoe 49 having an antimicrobial insole 50. FIG. 4 shows a close-up view of the insole 50 of FIG. 3.

In the embodiment of FIG. 4, the shoe insole 50 comprises a resilient layer or pad 51 such as formed by a closed-cell or open cell foam plastic material having a plurality of pores or reservoirs 52 formed therein. Each of the pores is filled with a composition comprising DMH and silver chloride in particles, preferably, powder form 54.

The presence of a fluid proximate the DMH and silver chloride powder 54 causes the release of silver ions into the fluid, where the fluid may be moisture resulting from foot perspiration. The release of silver ions can effectively kill or control microorganisms in the fluid while the releasing DMH into the fluid containing the silver ions increases the level of silver ions in the fluid. That is, the DMH and the silver acting together are more effective in killing microorganisms than if silver ions from the silver chloride were used alone since the concentration of silver in the fluid is greater. It is noted that a feature of the present invention is that DMH and silver chloride powder 54 compositions provide for long-term effectiveness of the shoe insole 50 as the DMH and silver chloride do not interact with each other to form the soluble complex in their dry form. Instead, the interaction between the DMH and silver chloride is initiated once the DMH and silver chloride comes in contact with a fluid source. That is, in the shoe environment, the DMH and silver chloride soluble complex is not formed until the presence of moisture resulting, for example, from foot perspiration or environmental fluid seeping into the shoe creating the ideal growth environment for both bacteria and fungus.

Referring to FIG. 4, shoe insole 50 also includes a fluid permeable, preferably fabric layer 53 secured to a surface of the resilient layer 51 and covering the openings or pores 52. In the embodiment of FIG. 4, layer 53 provides the dual purpose of not only maintaining the DMH and silver chloride powder 54 within pores 52 but also to absorb fluids and direct the fluids into pores 52 so that the DMH and silver chloride powder 54 can be activated to effectively kill or control microorganisms in the fluid. In alternative embodiments of the present invention layer 53 may also function to control release of the DMH and silver chloride powder 54 into the shoe as the shoe insole 50 is walked upon to further distribute the DMH and Silver chloride powder 54 within the shoe 49.

The DMH and silver chloride powder 54 may also include a desiccant having a high affinity for water such as calcium oxide or silica gel to further attract fluids to the DMH and silver chloride powder 54, anti-fungal compositions to further help in the control of diseases such as athletes' foot and other infections and optionally fragrances for odor control. Desirably, the articles should be sealable in a fluid-proof condition so that they can be stored for extended periods without substantial loss of activity prior to use.

In further regards to the resilient layer 51, the resilient layer 51 may also comprise various types of material commonly used as an impact-absorbing layer in shoe insoles or other compressible articles. Particularly suitable are foam rubber insole materials, such as rubber latex foams, polyurethane latex foams, polypropylene latex foams, butyl latex foams, and the like. Particularly preferred are closed-cell foamed thermoplastics formed from a number of known thermoplastic foam materials and blends thereof, such as polyethylene, ethylene vinyl acetate copolymers, cross-linked polyethylene, acrylics, polyvinyl chloride, polystyrene and the like. Such foamed materials can be obtained as pre-formed thermoplastic sheets, or alternatively, may be molded into a desired shape and foamed by nitrogen injection by a well-known technique. The pre-formed foam materials can be thermo-molded after softening in an oven in a conventional mold cavity.

It is noted that an alternative embodiment may comprise an anti-microbes spray containing a DMH-silver chloride complex formed by an interaction between the DMH and the silver ion donor such as silver chloride with or without a suitable carrier liquid applied as a liquid stream, fine vapor, mist, small drops, aerosol, or non-aerosol. The spray could be used for example to eliminate or control the growth of microorganisms in or about the surfaces of the shoe. The sprayable DMH-silver chloride complex may, optionally, include additional additives such as, e.g., a fragrance, water thickener, surfactant, dispersant, supplemental solvents, anti-static agent, colorant, etc. . . .

Another feature of the invention is that the antimicrobial agent may also be used as an additive incorporated into products that are applied to upon the human body including but not limited to deodorants, various feminine products, shampoo/conditioner, lipstick, facial creams, hand wipes, etc. . . . to help reduce microbes numbers either by reducing perspiration or by directly affecting the micro-organisms on the surface of the body as represented herein by skin. The antimicrobial product may be applied to the user's body in two forms, namely with the silver chloride particles and DMH particles in their separate form to provide for extended antimicrobial effects or in a soluble DMH-silver ion complex form to provide for instant antimicrobial effects.

When used in products that provide for the extended antimicrobial activities, such as a deodorant 55 shown in FIG. 5, a composition 56 that includes silver chloride particles and DMH particles is dispensed to a desired portion on the user's body such as the underarm areas or feet via a carrier such as but not limited to a skin-adhering polymer, various gels, and waxes. Once applied to the user's body, the silver chloride particles and DMH particles are maintained thereon until the user's body heats up and the user perspires, which will initiate the formation of the DMH-silver chloride complex. That is, when the user perspires, the silver chloride releases silver ions into the sweat fluid to kill microorganisms. The DMH is also release into the sweat fluid to form a soluble DMH-silver ion complex that is also effective in killing microbes. Once the user's body cools down and the perspiration dries the interaction between the DMH particles and silver chloride particles forming the soluble DMH-silver ion complex is halted due to the lack of a fluid source. The DMH and silver chloride particles remaining on the user's body will not interact with each other to form the soluble complex until the user perspires again thereby providing for extended antimicrobial effects. Example of other products that may provide for the extended antimicrobial effects include but is not limited to various type of cosmetic products including lip sticks, various facial creams, anti-bacterial/healing ointments, and bandages.

When used in products that provide antimicrobial properties, such as the hand wipes 57 shown in FIG. 6, the silver chloride and the DMH will be applied to the intended surface in their complex form. That is, silver chloride particles and DMH particles are first added to the hand wipes fluid solution. In the hand wipes fluid solution the DMH interacts with the silver to form the soluble DMH-silver ion complex 58 that is effective in killing microbes. As the DMH is maintained in the hand wipes fluid solution with the silver chloride, the DMH continuously interacts with the silver ions donated by the silver chloride particles thereby increasing the concentration microbes killing DMH-silver ion complex until the either the DMH or silver chloride particles are exhausted or until the hand wipes fluid solution is saturated with the microbes killing soluble DMH-silver ion complex. The hand wipes fluid solution containing the microbes killing soluble DMH-silver ion complex 58 is then placed into a dispensing container 60 housing a roll of wipes 59. The wipes 59 in the dispensing container are then soaked with the hand wipes fluid solution containing the microbes killing soluble DMH-silver ion complex 58 and are ready for use.

It is noted that the hand wipes fluid solution containing the microbes killing soluble DMH-silver ion complex 58 may also be used as an anti-microbes spray applied as a liquid stream, fine vapor, mist, small drops, aerosol, or non-aerosol. The may, optionally, include additional additives such as a fragrance, water thickener, surfactant, dispersant, supplemental solvents, anti-static agent, colorant, etc. . . .

Although not shown, the microbes killing soluble DMH-silver ion complex may also be incorporated into gel or solid products that provide for instant antimicrobial effect. Examples of such products are body washes, which may come in the form of a liquid, a paste, or a solid. Body washes in the present context includes liquid soaps, wash lotions, shower bath preparations, foam baths or hair shampoos which are applied to clean the skin or the scalp and hair and which are rinsed off with water. These products are different from the deodorant 55 of FIG. 5 and the hand wipes 57 of FIG. 6 in that the products are applied to the user's body in solid or gel form but with the silver chloride and the DMH additive in their complex form or microbes killing soluble DMH-silver ion complex form. The aforementioned may be accomplished for example through the encapsulation of the microbes killing soluble DMH-silver ion complex in small water dissolvable beads for gel-based body washes or within the confines of various water-soluble lipids for solid body washes. Once the beads or water-soluble lipids are dissolved during use, the microbes killing soluble DMH-silver ion complex will be release to provide for instant antimicrobial effects.

FIG. 7 shows an article of wear comprising a glove 70 having an exterior surface 71 containing a antimicrobial agent comprising a source of biocidal metal 72 and a compound 73 containing a hydantoin ring. In the embodiment shown the glove may have the antimicrobial agent on the outside or the inside of the glove or both. Having the antimicrobial agent on the outside will ensure that when moisture is proximate the outside the glove can be used to handle products without transferring harmful microorganisms. Having the antimicrobial agent on the inside will prevent growth of harmful microorganisms within the glove.

FIG. 8 shows a one-piece hand shaped sheet of material 75 with a antimicrobial agent comprised of a source of biocidal metal 77 and a source of hydantoins 76 for providing a antimicrobial area on one side of the hand shaped sheet while FIG. 9 shows an end view of the one-piece hand shaped sheet of FIG. 8 revealing that the one-piece hand shaped sheet of material includes an adhesive 78 for securing the material 75 to the user's hand. Such a device is well suited to applications where one may have to move between handling food and handling money which may contain harmful organisms. One may simple place the material 75 on the open hand and let the adhesive hold the material in place while a food product is being handled. The sheet of material 75 can then be quickly removed from the users hand to handle other items.

FIG. 10 shows an example of a body product such as a tube of lipstick 89 that is applied to the skin of a user with the body product including the antimicrobial agent incorporated into the solid lipstick 81 wherein the antimicrobial agent includes the source of biocidal metal ions and the compound contains a hydantoin ring.

Figure 11:
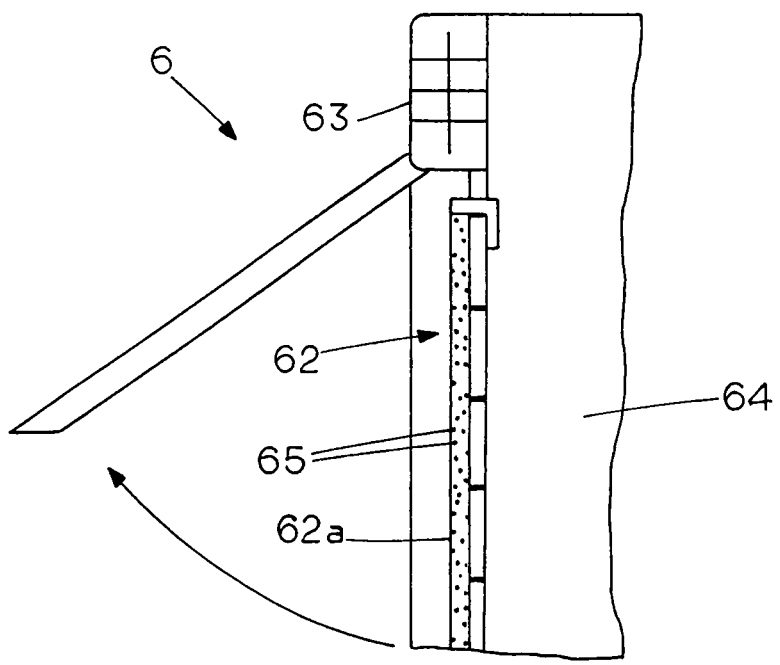
FIG. 11 shows a partial cross-sectional side view of an antimicrobial air-conditioner filter.

Another feature of the invention is that the sanitizer may be incorporated into secondary body products that indirectly affect a person through transfer of air between a source of harmful organisms and a person. That is, airflow can bring the harmful microorganisms into contact with a human through contaminated airflow. To help kill or control microbes growth in the fluid the antimicrobial agent can be incorporated at the source of the harmful microorganisms thereby rendering airflow safe. FIG. 11 shows a partial cross-sectional side view of the antimicrobial air-conditioner filter 62 having a composition that includes a source of biocidal metal and a compound containing a hydantoin ring which is incorporated into a traditional filter of an air conditioner unit 61. antimicrobial air-conditioner filter 62 is capable of cleaning, deodorizing, and providing anti-fungal, and anti-mold activity to an air conditioner. In the general operation of the air conditioner units, upon activation of a driving the fan (not shown), external air containing dusts, fluids and the like is drawn through the suction grill 63 into the air conditioner unit 61. The external air then arrives at a filter, which is located before the air condenser 64. The filter functions to remove dusts, fluids and the like from the external air before the air moves into the condenser 64 for cooling. In order to remove odors, some traditional filters have incorporated the use of activated carbon therein to deodorize the external air before the air moves into the condenser for cooling. However, the deodorizing filters that incorporate the activated carbon has problems in that a deodorization performance is poor and short-lived, and harmful microbes cannot be sterilized.

Although traditional air-conditioner filters function effectively to remove dust, and fluids and at time odors from the external air before the air moves into the condenser for cooling, one of the main problems associated with traditional air-conditioner filters is that as the filters remove fluids from the external air, the fluids starts to build up in the filters thereby providing a possible environment for bacterial growth. The present invention solves the aforementioned problem by providing for an improved air-conditioner filter 62 that incorporates the antimicrobial agent within the filter medium 62a of the air-conditioner filter 62. That is, an antimicrobial composition 65 comprising particles of silver chloride and DMH is incorporated into the filter medium, which may comprise either a woven or non-woven fabric such as for example polypropylene(PP) resin fiber or polyethylene(PE) resin fiber. The antimicrobial composition 65 is maintained within the filter medium 62a and activated in the presence of a fluid.

In use as the air-conditioner filter 62 remove fluids from the external air, fluid starts to build up in the filter medium 62a. The presence of the build-up of fluid causes the silver chloride particles to release silver ions into the fluid in the filter medium 62a to kill microorganisms. The DMH particles also release DMH into the fluid in the filter medium 62a to interact with the silver ions to form a soluble DMH-silver ion complex that is also effective in killing or control the growth of microbes.

Once filter medium 62a dries the interaction between the DMH particles and silver chloride particles forming the soluble DMH-silver ion complex is halted due to the lack of a fluid source. The DMH and silver chloride particles remaining in the filter medium 62a will not interact with each other to form the soluble complex until fluid starts to build up in the filter medium 62a again thereby providing for extended antimicrobial effects of the air-conditioner filter 62. In view of the aforementioned, unlike traditional air-conditioner filter, air-conditioner filter 62 functions not only to filter dusts and particulates but also to remove of odor cause by odor-producing microorganisms and/or sterilize microbes that are exposed to the air condition.

Figure 12:
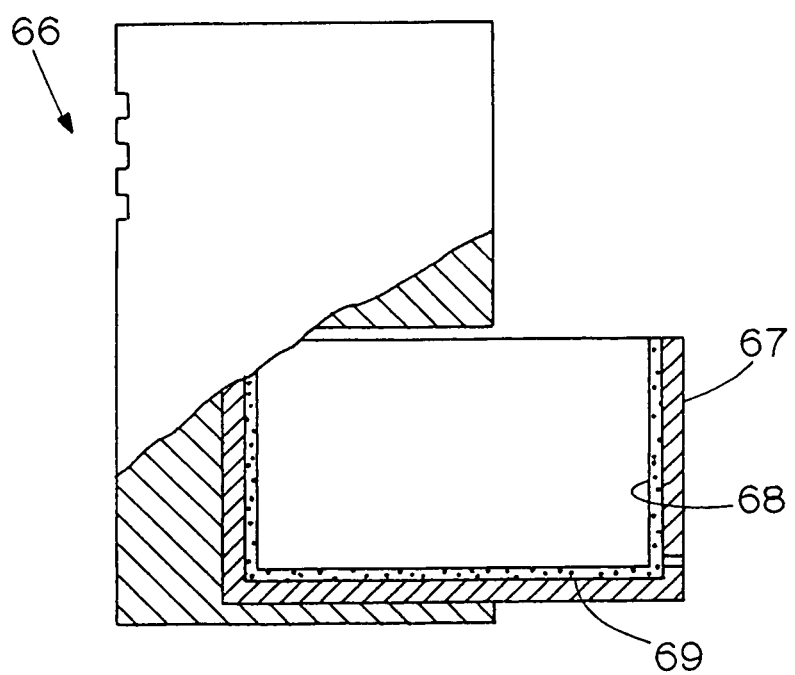
FIG. 12 shows a partial cross-sectional side view of an antimicrobial fluid collection pan.

FIG. 12 shows a partial cross-sectional side view of an antimicrobial fluid collection pan 67 having a composition that includes a source of biocidal metal and a source of hydantoins dispersibly incorporated in the form of a antimicrobial lining or coating 69 on an interior surface 68 of a fluid collection pan of a traditional dehumidifier 66. An example of one of the processes involved in forming the antimicrobial lining or coating 69 may comprise the combination of the silver chloride while in solution with an adhesive, and preferably a slow dissolving adhesive, to form an adhesive silver chloride solution. The adhesive and the silver chloride solution are then applied to the interior surface 68 of fluid collection pan 67. DMH particle is then added to the adhesive silver chloride mixture as the adhesive is cured to produce the antimicrobial lining or coating 69 containing the silver chloride particles and DMH particles that are available for releasing into the body of fluid collected by fluid collection pan 67 to aid in the disinfection or antimicrobial effects of the body of fluid collected by fluid collection pan 67. A suitable material for adhesively securing the silver chloride proximate the carrier is commercially available gelatin, which can be cross-linked with an aqueous solution of formaldehyde or glutaraldehyde to form a non-soluble, water penetrable matrix on the exterior surface of the carrier. Other suitable non-soluble water porous adhesive matrixes are polyvinyl acetate, polyurethane, epoxy resin, polyvinyl alcohol and polyvinyl acetate.

In use, as the antimicrobial lining or coating 69 comes into contact with the fluid collected by fluid collection pan 67, the antimicrobial lining or coating 69 releases silver ions into the fluid collected by fluid collection pan 67 to effectively kill or control the growth of microorganisms. The DMH then the biocidal effectiveness of the silver by forming a complex with the silver to allow the silver to remain soluble to a higher degree thereby retaining the silver's antimicrobial activity.

A feature of the antimicrobial lining or coating 69 is that the use of a slow dissolving adhesive allows the antimicrobial lining or coating 69 to release the silver chloride and the DMH at a slow rate for more of a time-controlled release. That is, the silver chloride and the DMH located within the antimicrobial lining or coating 69 are not release, i.e. dissolved in the body of fluid collected by fluid collection pan 67 until the silver chloride and DMH located on the outer layer of the antimicrobial lining or coating 69 are released into the body of fluid collected by fluid collection pan 67. Use of the antimicrobial lining or coating 69 thus is ideal for fluid collected by fluid collection pan 67 as the fluid collected by fluid collection pan 67 antimicrobial effects do not require immediate antimicrobial effects but instead requires lengthy or extended antimicrobial effects. A feature of the antimicrobial lining or coating 69 is that the antimicrobial lining or coating 69 allows for prolong use as the DMH and silver chloride do not interact with each other to form the soluble complex without the presence of the fluid. Instead, the interaction between the DMH and silver chloride is initiated once the DMH and silver chloride comes in contact with a fluid source.

Figures 13, 14:
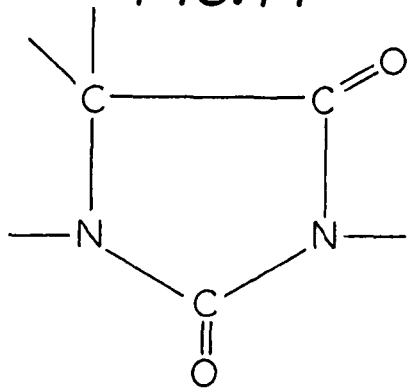
FIG. 13 shows the concentrations of silver with and without the addition of DMH.
FIG. 14 shows a diagram of a hydantoin ring.

FIG. 14 shows a schematic of the structure of a hydantoin ring with carbon and nitrogen atoms joined in a five-sided ring. An oxygen atom is attached to two of the carbons in the hydantoin ring. The lines extending from the third carbon atom and the nitrogen atom indicate that other atoms could be attached thereto. For example, in a compound containing a hydantoin ring, such as DMH (5,5-dimethylhydantoin), two methyl groups would be attached to the carbon atom an a hydrogen atom would be attached to each of the two nitrogen atoms.

It has been found that compounds containing a hydantoin ring such as 5,5-dimethylhydantoin (DMH), have the qualities to interact with metal ion donors including silver metal ion donors to increase the solubility of the silver in a water environment and the antimicrobial or disinfection process. While a number of compounds with a hydantoin ring may be used as a practical matter one may want to avoid those compounds where the group or groups on the compound may have an adverse effect on the antimicrobial product. Some compounds containing a hydantoin ring may have antimicrobial effects, however, the tests reveal that if the compound containing a hydantoin ring has no antimicrobial effect when used alone the use of the compound with the hydantoin ring in conjunction with the known metals that have antimicrobial agent produces enhanced antimicrobial activity through elevated levels of metallic ions.

Examples of other well known compounds wherein the compound contains a hydantoin ring include that may include other antimicrobial effects silver dimethylhydantoin 1-hydroxymethyl-5,5-dimethlyl hydantoin, glycolyurea and Copper hydantoin, Hydantoin-5-acetic acid, and Imidazolidines including parabanic acid, 2-Thiohydantoin, hydantoin purum, hydantoin, 1-Aminohydantoin hydrochloride, 2-Imidazolidone, 2-Imidazolidone purum, 2-Imidazolidinethione, 2-hydrazino-2-imidazoline hydrobromide, 2-oxo-1-imidazolidinecarbonyl chloride, 1-methylhydantoin, 5-methylhydandtoin, 2-imidazolidone-4-carboxylic acid, allantoin, allantoin purum, creatinine anhydrous,-creatinine biochemika, creatinine hydrochloride, 2-methyl-2-imidazoline, 2-methylithio-2-imdazoline hydrodide, 3-brmo-1-chlor-5-5-dimethlyhydantoin, 1-3-dibromo-5,5-dimethlyhydantoin purium, 1-3-dichlorol-5,5-dimethylhydantoin, 1,3-dichlor-5,5-dimethylhydantoin, hydantoin-5-acetic acid. 2-chlorocarbonyl-1-methanesulfonyl-2imidazolidinone. 5,5-dimethylhydantoin purum. 5,5-dimethylhydantoin, 2-imino-1-imidaolidineacetic acid, 1,3-dimethyl-2-imidazolidinone puriss, 1,3-dimethly-2-imidazolidinone purum, 1,3-dimethyl-2-imidazolidinone, 1-(2-hydroxyethyl)-2-imdazolinone, 1,5,5-trimethlylhydantoin, 5-ethyl-5-methylhydantoin, 2-phenyl-2-imidazoline purum, 2-(4,5-dihydro-1h-imidazoyl)-2-phenol, 4-(4,5-dihydro-1H-imidazol-2yl) phenylamine, 5-methyl-5-phentylhydantoin, 2-benzylimidazoline, 4-(4-methyl-4,5-dihydro-1H-imidazol-2-yl)phenyl, Imidazolidinyl urea, 4-hydroxymephenyloin, triethoxy-3-(2-imidazolin-1-yl)propysiliane purum, 1,(p-tosyl)-3,4,4-trimethylimidazolidine, naphazoline nitrate purisss, 5,5,diphenyl-2-thiohydantoin, 5-(4-hydroxyphenyl)-50phenylhydantion, 5-(p-methyl phenyl)-5-phenyhydantoin, 1,3,bisbensyl-2-oxoimidazoline-4,5-dicarboxylic acid. Other examples of hydantoins are listed in European patent EP0780125 which is herby incorporated by reference. The above list compounds with a hydantoin ring is illustrative and no limitation thereto is intended.

A silver ion donor in the presence of a compound containing a hydantoin ring such as DMH has a level of free silver higher than anticipated when compared to the silver ion donor in a water environment without the DMH. The results suggest that DMH s the solubility of the silver thereby increasing the biocidal effectiveness.

In order to verify that a compound containing a hydantoin ring, such as DMH, interacts to increase the solubility of insoluble silver in a water environment, a test was performed using either silver chloride or silver bromide as the donor of silver metal ions. The test demonstrated the level of silver in a water environment when DMH is used in combination with a source of silver ions.

EXAMPLE

Silver bromide was initially prepared from a saturated sodium bromide solution, combined with silver nitrate in solution. The yellow precipitate, silver bromide, was than purified by filtration and washing. Additionally, the solid was allowed to dry before use.

A buffer system having a pH of 7.41 was prepared by adding Fisherbrand® potassium phosphate monobasic-sodium phosphate dibasic buffer to 2 Erlenmeyer flasks filled with 1000 mL of purified water. The first flask was treated with 1.12 grams of 5,5-dimethylhydantoin (DMH) and marked solution "C" (with DMH) and the second flask was left untreated and marked solution "D" (without DMH) for control. In regards to the 5,5-dimethylhydantoin (DMH), the 5,5-dimethylhydantoin (DMH) comprised 97% reagent grade was obtained from Aldrich®(CAS No. 77-71-4, Cat. No. D161403-1KG).

After the initial set-up, approximately 0.10 grams of dried silver bromide was introduced into a dialysis tubing (Fisherbrand®, 45 mm, MWCO 12,000-14,000) along with purified water. The ends of the dialysis tubing were clamped to contain the silver bromide and purified water. Next, the outside of the dialysis tubing was rinsed several times to ensure that silver bromide residue was not on the outside of the dialysis tubing. A string was then tied to one clamp, and one tube was introduced into each flask. A magnetic stir bar was used to mix the solutions.

During the period of the test, a 100 ml sample were removed from solution "D" (without DMH) and solution "C" (with DMH) at weekly intervals and analyzed for their pH using Orin Perphect Meter 370 and analyzed for their silver ion concentrations using atomic absorption spectrometry.

FIG. 13 shows a table containing a list of the dissolved silver concentration, in parts per billion (ppb) obtained from the 100 ml samples for solution "D" (without DMH) and solution "C" (with DMH) at each of their respective weekly time intervals. The average concentration of dissolved silver for solution "C" (with DMH) was 86 ppb while solution "D" (without DMH) had an average concentration of dissolved silver of 4.7 ppb.

A week after the start date, the concentration of dissolved silver for solution D (without DMH) was at 4.3 ppb, while the concentration of dissolved silver for solution C (with DMH) was at 2.8 ppb. By the end of the testing, 6 weeks later, the concentration of dissolved silver for solution C (with DMH) had increase to 220 ppb, while the concentration of dissolved silver for solution D (without DMH) was 7.1 ppb. That is, by the end of the 6 weeks test, the concentration of dissolved silver was at least 30-fold greater in solution C (with DMH) then for solution D, (without DMH).

In summary, the results of the above testing confirmed that in a solution containing silver bromide, the presence of compound containing a hydantoin ring, such as DMH, leads to a higher dissolved silver concentrations than compared to a control solution containing silver bromide without the presence of the DMH. These results suggest that compounds containing a hydantoin ring interact with silver to form a soluble complex even if the source of silver comprises an extremely insoluble silver salt such as silver bromide.

In regards to generating a level of silver ions, the King Technology, Inc. Frog® Mineral Cartridge provides one method of delivering silver ions in the form of solid silver chloride (AgCl) distributed over a porous matrix. The water releases the soluble silver ions into the water environment with. DMH resulting in the formation of ionic-hydantoin structures. It would be anticipated that soluble silver ions would be depleted from the water environment through the formation of silver bromide, an insoluble salt. However, as shown in FIG. 13 after the DMH was added to the water environment, the actual silver concentrations were higher than the calculated theoretical silver concentration.

It is noted that various insoluble or slightly soluble transition metal salts may also be used in the present invention as a source of silver ions. Examples of insoluble or slightly soluble transition metal salts suitable for use in the present invention include, but are not limited to, AgCl, AgBr, AgI, $Ag_2S$, $Ag_3PO_4$, $NaAg_2PO_4$, CuS, and $NaCuPO_4$. Other examples of silver compounds include, but are not limited to, $AgNO_3$, $Ag_2CO_3$, AgOAc, $Ag_2SO_4$, $Ag_2O$, $[Ag(NH_3)_2]Cl$, $[Ag(NH_3)_2]Br$, $[Ag(NH_3)_2]I$, $[Ag(NH_3)_2]NO_3$, $[Ag(NH_3)_2]_2SO_4$, silver acetoacetate a silver benzoate, a silver carboxylate, silver amine complexes such as $[Ag(NR_3)_2]X$, where R is an alkyl or aryl group or substituted alkyl or aryl group and X is an anion such as, but not limited to, $Cl^-$, $Br^-$, $I^-$, $OAc^-$, $NO_3^-$ and $SO_4^{2-}$.

Although various sources of silver have been described it should be understood that the source of silver ions may be metallic silver or a metallic silver alloy. Similarly, other heavy metals which have antimicrobial properties such as zinc or copper may be used as the source of the biocidal metal ions.

In the example, the preferred level of the DMH present in the liquid is at least 5 ppm DMH and preferably between 5 and 25 ppm DMH to cooperate with the source of silver cooperating to maintain a level of silver ions present in the amount of at least 1 to 3 ppb and/or alternatively cooperating to maintain a level of silver ions present to sustain a standard plate count at 35 degrees F. of less than 200 colonies per milliliter. However, as the test results show the level of silver can be increased if greater antimicrobial effect is desired.

As described herein the antimicrobial agent can be placed on or in a product in an inactive condition. When an activating fluid, such as water, comes into contact with the antimicrobial agent the effectiveness of the antimicrobial agent is increased to thereby kill harmful microorganisms. The activating fluid can come from various sources including body fluids as well as moisture from the air. While the compound containing the hydantoin ring effective coacts with a source of heavy metal ions such as silver ions one may also use compounds containing a hydantoin ring which have antimicrobial properties. Examples of compounds containing a hydantoin ring which have antimicrobial properties include the group consisting of Bromochlorodimethylhydantoin (BCDMH) Dichlorodimethylhydatoin (DCDMH) and Silverdimethylhydantion (AgDMH).

We claim:

1. An article of skin wear for carrying harmful microorganisms that can directly or indirectly transmit the harmful organism to a human comprising:
    an article surface for growth of harmful microorganism;
    an antimicrobial agent including a source of biocidal metal ions proximate said article surface; and
    a compound containing a hydantoin ring proximate said article surface, said compound containing said hydantoin ring and said antimicrobial agent maintained in a non-complex state until the article surface is in use.

2. The article of skin wear of claim 1 wherein the article comprises an article of wear and the compound containing a hydantoin ring lack antimicrobial properties.

3. The article of skin wear of claim 1 wherein the source of biocidal metal ions comprise a source of silver ions and the compound containing a hydantoin ring comprises 5,5-dimethylhydantoin (DMH).

4. The article of skin wear of claim 1 wherein the source of biocidal metal ions comprise silver chloride and the compound containing a hydantoin ring comprises DMH.

5. The article of skin wear of claim 4 wherein the article of skin wear comprises a deodorant, feminine products, shampoo/conditioner, hand or facial wipes, or a lipstick.

6. The article of skin wear of claim 1 wherein the article comprises an article of footwear, an article of clothing, or a fabric.

7. The article of skin wear of claim 1 wherein the liquid is water and the concentration of compound containing the hydantoin ring is at least 5 ppm and the compound containing a hydantoin ring is selected from group consisting of Bromochlorodimethylhydantoin (BCDMH), and Dichlorodimethylhydantion (DCDMH).

8. The article of skin wear of claim 1 wherein the compound containing the hydantoin ring is DMH and the concentration of the DMH in the liquid is at least 5 ppm but less than 25 ppm.

9. A method of limiting human exposure to harmful microorganisms comprising:
    applying an antimicrobial agent containing a source of biocidal metal ions and a compound containing a hydantoin ring to an article surface for direct or indirect human contact;
    maintaining the antimicrobial agent and the compound containing the hydantoin ring in a non-complex state until the article surface is in use; and
    using the article surface by introducing an activating liquid to the source of biocidal metal ions and the compound containing a hydantoin ring to bring biocidal metal ions and the compound containing a hydantoin ring into solution to thereby release biocidal metal ions to kill microorganism in contact with the article surface.

10. The method of claim 9 wherein the source of biocidal metal ions is silver chloride and the compound containing a hydantoin ring is DMH and wherein sufficient DMH is added to bring the concentration of DMH in the activating fluid to at least 5 ppm.

11. The method of claim 9 wherein applying the antimicrobial agent comprises incorporating the source of biocidal metal ions and a compound containing a hydantoin ring directly into a body affecting product.

12. The method of claim 9 wherein the source of biocidal metal ions and the compound containing a hydantoin ring are brought into an active antimicrobial state through the presence of liquid.

13. The method of claim 12 wherein the source of biocidal metal ions and the compound containing a hydantoin ring are brought into an active antimicrobial state through the presence of body fluids.

14. The method of claim 13 wherein the source of biocidal metal ions is silver chloride and the compound containing a hydantoin ring is DMH.

15. The method of claim 9 wherein the compound containing a hydantoin ring is selected from the group consisting of Bromochlorodimethylhydantoin (BCDMH), Dichlorodimethylhydatoin (DCDMH) and Dibromodimethylhydantoin (DBDMH).

16. The method of claim 9 including the step of extending a sanitation life of the source of biocidal metal ions and the compound containing the hydantoin ring by removing the activating liquid from the source of biocidal metal ions and the compound containing the hydantoin ring to halt the interaction between the biocidal metal ions and the compound containing the hydantoin ring.

17. The method of claim 9 wherein the source of activating liquid comprises a body fluid.

18. The method of claim 9 wherein the compound containing the hydantoin ring is maintained at least 5 ppm in the activating liquid.

* * * * *